(12) United States Patent
Baaske et al.

(10) Patent No.: US 10,016,261 B2
(45) Date of Patent: Jul. 10, 2018

(54) OCCLUSION DETERMINATION DEVICE

(71) Applicant: Ivoclar Vivadent AG, Schaan (LI)

(72) Inventors: Thomas Baaske, Grabs (CH);
Christian Frei, Naturns (IT); Frank Zimmerling, Schaan (LI); Ronny Watzke, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/435,572

(22) PCT Filed: Dec. 17, 2013

(86) PCT No.: PCT/EP2013/076895
§ 371 (c)(1),
(2) Date: Apr. 14, 2015

(87) PCT Pub. No.: WO2014/095857
PCT Pub. Date: Jun. 26, 2014

(65) Prior Publication Data
US 2015/0327967 A1    Nov. 19, 2015

(30) Foreign Application Priority Data

Dec. 17, 2012    (EP) ...................................... 12197441

(51) Int. Cl.
| | |
|---|---|
| *A61C 19/04* | (2006.01) |
| *A61C 13/08* | (2006.01) |
| *A61C 19/05* | (2006.01) |
| *A61C 13/00* | (2006.01) |
| *A61C 13/01* | (2006.01) |

(Continued)

(52) U.S. Cl.
CPC ............ *A61C 13/081* (2013.01); *A61C 13/00* (2013.01); *A61C 13/0006* (2013.01); *A61C 13/01* (2013.01); *A61C 13/097* (2013.01); *A61C 13/1006* (2013.01); *A61C 13/1016* (2013.01);
(Continued)

(58) Field of Classification Search
CPC ..... A61C 13/00; A61C 13/0004; A61C 13/01; A61C 19/045; A61C 13/0006; A61C 19/05; A61C 13/081; A61C 13/097; A61C 13/1006; A61C 13/1016
See application file for complete search history.

(56) References Cited

U.S. PATENT DOCUMENTS 1,052,806 A  *  2/1913  Evans .................. A61C 19/045
                                                    433/73
3,200,497 A  *  8/1965  Goodfriend .......... A61C 11/022
                                                    433/214

(Continued)

FOREIGN PATENT DOCUMENTS

| FR | 2548532 A1 | 1/1985 |
|---|---|---|
| JP | S54137294 A | 10/1979 |
| JP | S568048 A | 1/1981 |

*Primary Examiner* — Ralph Lewis
(74) *Attorney, Agent, or Firm* — Ann M. Knab; Thad McMurray

(57) ABSTRACT

The invention relates to an occlusion determination device (10), with a bite frame (34) and an extraoral bracket (12) which are connected together, wherein a reference element has at least one vertical leg (19, 21) and at least one horizontal leg (14, 16) and is connected by way of a bipupillar linkage (24) to the bite frame (34). The reference element is designed as an extraoral bracket (12) which extends vertically offset from the bite frame (34).

24 Claims, 10 Drawing Sheets

(51) Int. Cl.
*A61C 19/045* (2006.01)
*A61C 13/36* (2006.01)
*A61C 13/097* (2006.01)
*A61C 13/093* (2006.01)

(52) U.S. Cl.
CPC ............ *A61C 19/045* (2013.01); *A61C 19/05* (2013.01); *Y10T 29/49567* (2015.01)

(56) References Cited

U.S. PATENT DOCUMENTS

| | | |
|---|---|---|
| 4,261,696 A | 4/1981 | Hobo |
| 5,020,993 A | 6/1991 | Levandoski |
| 5,385,470 A | 1/1995 | Polz |
| 6,152,731 A | 11/2000 | Jordan et al. |
| 2008/0057466 A1 | 3/2008 | Jordan |
| 2011/0217674 A1 | 9/2011 | Hanewinkel et al. |

\* cited by examiner

OCCLUSION DETERMINATION DEVICE

CROSS-REFERENCE TO RELATED APPLICATIONS

This application is a National Stage application of International patent application PCT/EP2013/076895 filed on Dec. 17, 2013, which claims priority to European patent application No. 12 197 441.4 filed on Dec. 17, 2012, the disclosures of which are incorporated herein by reference in their entirety.

TECHNICAL FIELD

The invention relates to an occlusion determination device having a bite frame and an extraoral bracket which are connected to one another, wherein a reference element includes at least one vertical leg and at least one horizontal leg and is connected with the bite frame by way of a bipupillary joint.

BACKGROUND OF THE INVENTION

Devices for the transmission of patients' data for the production of prostheses have long been known. Thus, DE 33 47 830 A1 discloses a corresponding device having a bite fork in which the reference bracket is provided with a scale via which the horizontal offset relative to the condylar joint axis is said to be determinable. According to page 5, this solution is based on a parallel extension of the occlusal plane to the bipupillary line.

However, in fact there can be a slight angular deviation and therefore it has become known to introduce a so-called bipupillary joint which takes account of said angular deviation. An example of a solution of this type is known from DE 30 32 913 A1.

The joint of said solution allows for an adjustment of the bite fork around a horizontal axis which extends perpendicularly to the condylar axis; however, no detection of the angular position is provided.

Numerous further corresponding devices have been suggested. It is referred to the more recent document U.S. Pat. No. 5,154,608 A1 which shows a device which serves to carry out an occlusion analysis and which comprises corresponding scales for the detection of the horizontal offset, as can be seen from FIG. 3 and the associated description, for instance.

However, in dental practices reference brackets are still used which are connected to bite forks and referred to as a bite fork kit, either via a joint or integrally, wherein the lengths of the bite fork kits are often reduced. In many cases the bite fork kits are formed from strips of sheet metal which extend horizontally. The dentist or optionally the dental technician can decide himself if he wants to bend the strips of sheet metal according to his desire or "extend" them using a small piece of wood until the condylar joint is reached. Solutions of this type are cost-effective; however, they are unsatisfactory in terms of ergonomics and accuracy of fit.

The plane, referred to as the Camper's plane, is known to run through the subnasal point and tragus. In many cases it is considered to be parallel to the occlusal plane, however, on closer inspection angular deviations can also be determined which differ from patient to patient.

In case of toothless patients, a wax template is used which is set to a medium value as an experience value and an occlusion determination device can be used for this purpose.

The occlusion determination devices known hitherto can only detect angular deviations in terms of an angle transverse to the condylar joint direction, i.e. corresponding to the bipupillary joint, if a corresponding angular detection, such as with a scale and a pointer, is realized.

Furthermore, auxiliary devices for articulators have been suggested which comprise scales which are supposed to take account of any deviations from usual values. In some cases, auxiliary brackets are used in this connection.

SUMMARY OF THE INVENTION

In contrast, the invention is based on the task of providing a simple, easy-to-use occlusion determination device according to the preamble of claim 1, but which can detect a plurality of patient-specific characteristics without having to fear operating errors due to a plurality of adjustment possibilities.

This task is inventively solved by claim 1. Advantageous developments may be taken from the subclaims.

The features of the inventive occlusion determination device facilitate an accurate and easy detection of the individual occlusal plane of a patient without an expensive implementation and application of the inventive occlusion determination device. By vertically offsetting the extraoral bracket its ends point towards the tragion and/or towards the condylar joints, such that an orientation of the extraoral bracket relative to the known shortened embodiment is simplified, in this respect. For this purpose, the length of the side leg of the extraoral bracket amounts to between 7 cm and 23 cm, preferably to about 15 cm for adults. In this respect, it is harmless if the ends of the extraoral bracket project beyond the tragus.

The vertical offset between the occlusal plane and the inventively arranged extraoral bracket is preferably set to a fixed value of between 20 and 30 mm and amounts to an average value of 25 mm. This corresponds to the typical offset between occlusal plane and Camper's plane.

Alternatively, it is possible to render the vertical offset adjustable; however, the "zero position" of the adjustment will then amount to 25 mm; the adjustment scale can then extend over a range of between 20 mm and 30 mm, for instance.

According to the invention, a bipupillary joint known per se which is formed at the center of the bottom centrically at the front of the occlusion determination device can determine, detect and measure the angle between the bipupillary line and the occlusal plane. For this purpose, a pointer, a rod or any other element extending vertically to the top is provided according to an inventively favorable manner which is fixedly connected to the extraoral bracket and extends precisely vertically relative to it. Now, the pointer is preferably oriented towards a central point in the sagittal plane of the patient.

For this purpose, a suitable point can be marked on the nose or forehead of the patient, for instance using a water-soluble felt-tip pen, and the pointer will then be oriented towards this point.

According to the invention it is favorable that a meter pointer is attached to the bipupillary joint together with a scale which pointer facilitates the detection of the angular offset between the occlusal plane and the bipupillary line, namely around the horizontal axis in the sagittal plane. The Camper's plane extends typically in a parallel fashion relative to the bipupillary line. In this connection, the meter pointer can either be attached to the bite frame or to the extraoral bracket—and therefore to the pointer—and the scale to the respective other part. Preferably, the scale is scaled in angular degrees and extends circularly in a way known per se.

According to the invention, the angular deviation around the mentioned axis in the sagittal plane can be determined more accurately than up to now in terms of the long "lever arms" of the extraoral bracket, wherein it is to be understood that the angular detection can be carried out in any desired way, for instance using a combination of meter pointer and scale but also using a digital display corresponding to those digital displays in electronic caliper gauges, or using a strain gauge and in this way via remote detection.

In a further advantageous embodiment it is provided to provide a Camper's joint in the area of the bite frame. The axis of this Camper's joint is positioned in the frontal plane and extends parallel relative to the condylar joint axis in this connection. The Camper's joint can inventively detect and measure the inclination of the Camper's plane relative to the occlusal plane. For this purpose, the Camper's joint comprises a meter pointer and a scale which are each attached to opposite joint parts. With the help of this, the bite frame can be pivoted with respect to the extraoral bracket around this axis and the angular position around this axis can be detected.

For detection purposes, the bite frame is equipped with a bite fork. When the bite fork is introduced into the mouth of the patient, it extends in the occlusal plane.

Therefore, when using the inventive occlusion determination device, the inclination of the occlusal plane with respect to the Camper's plane can be detected preferably in two dimensions, whereby the extraoral bracket serves as a reference element.

It is to be understood that the joint parts of both inventive joints can be pivoted against each other but, through static friction, can remain in the pivot position which has been adjusted. In this way, each joint remains in the set position when the bite fork is taken out of the patient's mouth such that the angular values can be easily read with the help of the respective meter pointer and the associated scale.

Alternatively, the joints can also be provided with a knurled nut which facilitates a fine adjustment of the pressure force of the joint parts against each other and also fixation.

Instead of the bite fork, the bite frame can also be provided with a receptacle for an impression compound carrier, and then detection can be carried out directly upon impression taking. An impression tray can for instance be used as an impression compound carrier or a Centric Tray of Ivoclar Vivadent AG.

According to the invention it is favorable if the parts of the occlusion determination device are punched or made of metal, preferably of strips of sheet metal. In this way, the entire occlusion determination device can be autoclaved and is correspondingly easy to sterilize.

Knurled nuts or suitable screw bolts facilitate the exchange or separation of joint parts from one another, if necessary, and this simplifies manageability.

Different jaw situations of individual patients can be taken into account by using the bite frame having changeable bite forks and/or impression compound carriers. As the extraoral bracket is attached to the remaining occlusion determination device via a screw bolt, it is also possible to have ready and apply different sizes, if applicable, in this connection.

BRIEF DESCRIPTION OF THE DRAWINGS

Further advantages, details and features may be taken from the following description of the invention in conjunction with the drawings.

DETAILED DESCRIPTION

Figure 1:
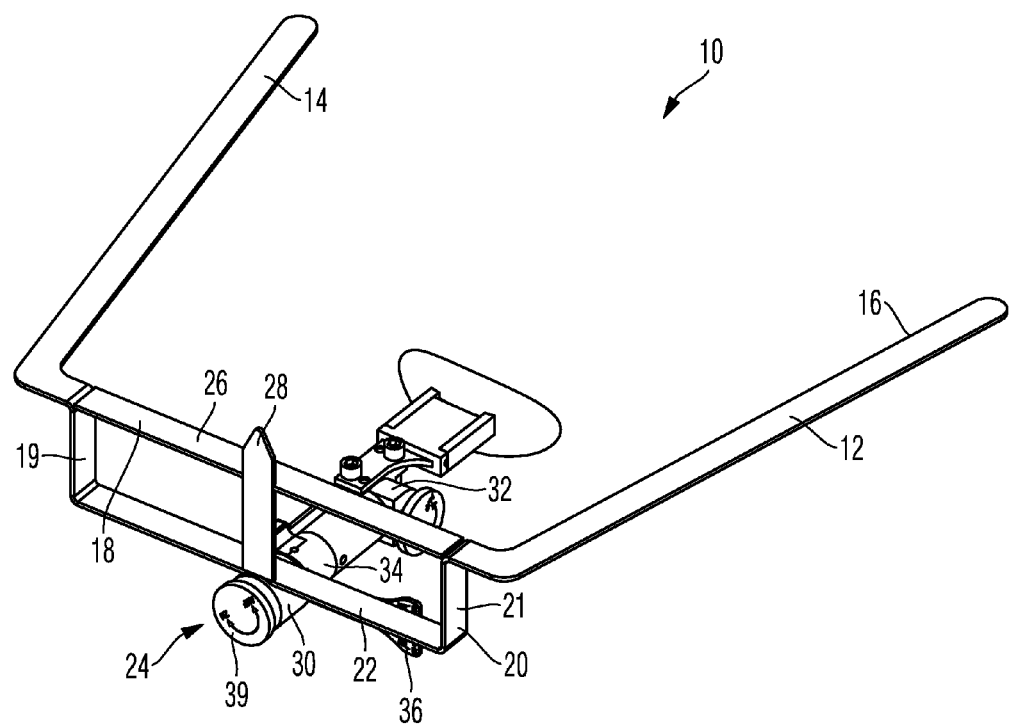
FIG. 1 shows a schematic perspective view of a first embodiment of an inventive occlusion determination device.

The occlusion determination device 10 illustrated in FIG. 1 comprises an extraoral bracket 12 as a reference element which extends in a substantially U-shaped manner and comprises two side legs 14, 16 and a center leg 18 for this purpose. The side legs 14 and 16 extend divergently from one another at an angle of about 25° to each other.

In a modified embodiment of the inventive occlusion determination device, not illustrated herein, the side legs 14 and 16 are each articulated with respect to the center leg 18. The respective joint can be a very simple joint and can, for instance, comprise two bores which are provided with ends of side and center legs facing each other. Said bores are in alignment with each other, and a suitable fastening element, such as a rivet, extends through these bores.

The adjustability can be limited in any suitable way by means of respective stops, for instance to an angular range of 45° to 90°, between the center leg 18 and the associated side leg 14 or 16, respectively.

The extraoral bracket 12 is formed in the form of a metal strip, for example made of stainless steel. In the exemplary embodiment illustrated, the metal strip comprises a width of 8 mm and a thickness of 1 mm, such that the desired inherent stiffness is given.

Alternatively, the extraoral bracket 12 and, if necessary, the remaining occlusion determination device can be made of a rigid plastic material, if needed of a fiber-reinforced plastic material, or of any other suitable material which can be disinfected easily.

The center leg 18 of the extraoral bracket 12 comprises a height offset portion 20 which also consists of steel strip and basically has a rectangular shape. In this respect, the height offset portion 20 forms a kind of frame for the extraoral bracket 12. The height offset portion 20 comprises two vertical legs 19 and 21. In the exemplary embodiment illustrated the steel strip is bent in the vertical direction, i.e. like an upright U, and a further steel strip 26 is welded between the ends of the side legs of said U which basically forms a substantial part of the horizontal center leg 18 of the extraoral bracket 12.

The height offset portion comprises a connection leg 22 to which a bipupillary joint 24 is mounted. A pointer 28 extends between said connection leg 22 and the steel strip 26 which is welded in. The pointer 28 extends to the top, substantially beyond the steel strip 26. While in the illustration according to FIG. 1 the pointer 26 comprises a length of only about 4 cm, it is to be understood that the length of the pointer can be increased substantially, for instance to 10 cm, if necessary.

The height offset between the connection leg 22 and the steel strip 26 which is in line with the side legs 14 and 16 of the extraoral bracket 12 amounts to 25 mm in the exemplary embodiment illustrated; another value of between 18 mm and 32 mm can also be used, if required.

The bipupillary joint 24 comprises a joint part 30 connected to the connection leg 22 and a joint part 34 connected to a bite fork connection 32. In this way, the joint part 30 is connected to a meter pointer not illustrated in FIG. 1, and the joint part 34 to a scale 36 which is used to guide the meter pointer of the bipupillary joint 24.

A knurled nut 39 facilitates a fixing and releasing of the joint, corresponding to the direction of rotation "open" or "close", as is indicated on the knurled nut 39.

Figure 2:
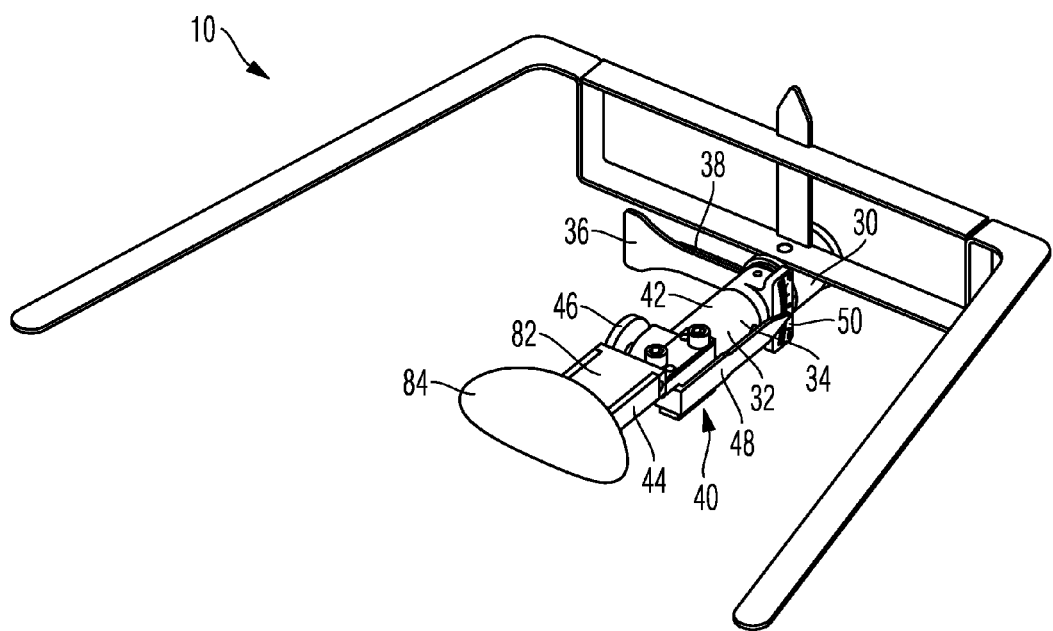
FIG. 2 shows the occlusion determination device according to FIG. 1 in another perspective view.

FIG. 2 shows the occlusion determination device 10 in a perspective rear view in the embodiment according to FIG. 1. Here, the same reference numerals refer to the same parts, as is also the case in all further Figures.

As can be seen from FIG. 2, a meter pointer 38 is assigned to the joint part 30 and is connected to it in a torque-proof manner. The scale 36 is connected to the joint part 34, and it is understood that the arrangement can also be chosen the other way round.

In an inventively particularly preferred embodiment the bite frame 34 comprises a further joint, namely the Camper's joint 40. The Camper's joint 40 in turn consists of a first part 42 in the form of a pin and a second part 44 which are screwed together by a knurled nut 46. The position or setting of the knurled nut 46 makes possible to set the friction force of the parts 42 and 44 to one another.

In this exemplary embodiment part 44 is connected to a second meter pointer 48, and part 42 to a second scale 50.

Reading the position of the meter pointer 48 on the scale 50 permits the detection of the angular position at the Camper's joint 40 the axis of which extends parallel to the condylar axis.

The bite frame 34 further comprises an alternating connection 82 which receives a receptacle 84 for an impression compound carrier (e.g. impression tray, Centric Tray) in the embodiment according to FIG. 2.

Figure 3:
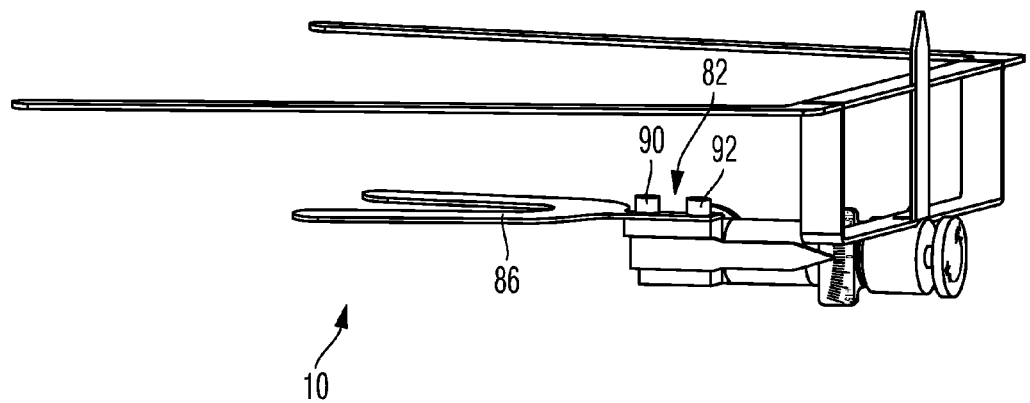
FIG. 3 shows a further embodiment of an inventive occlusion determination device (also in a perspective view)

FIG. 3 illustrates that the occlusion determination device 10 can also be provided with a bite fork 86 instead of the receptacle 84. For this purpose, the alternating connection 82 makes possible to release two bolts 90 and 92—or respective nuts in another embodiment—to select and install the respective connection piece and then to retighten the bolts 90 and 92. The height and angular position is predefined exactly by the connection surface formed here such that the occlusal plane is always detected accurately even with bite forks of different sizes.

Figure 4:
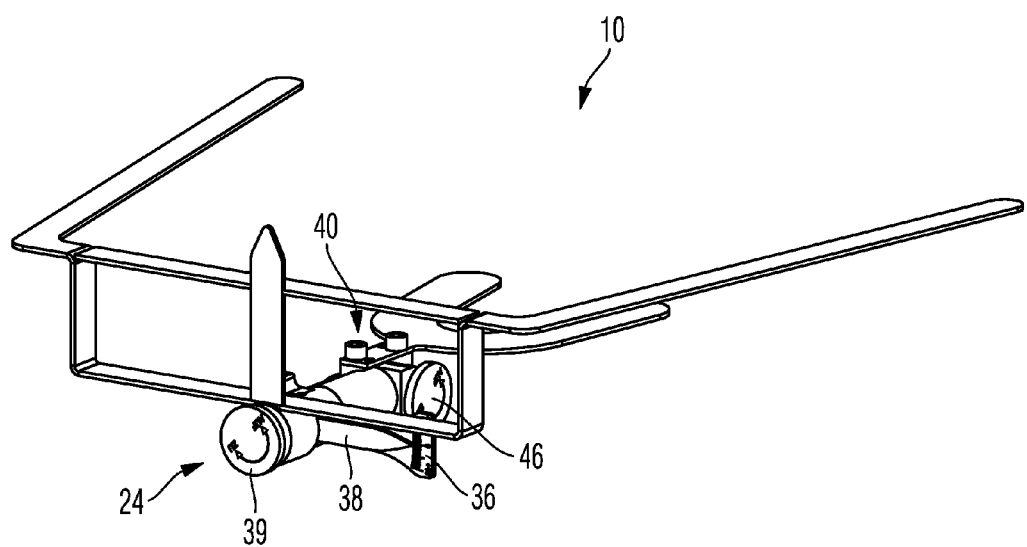
FIG. 4 shows the occlusion determination device according to FIG. 3 in another perspective view.

FIG. 4 shows that similar knurled nuts 39 and 46 can be used for the bipupillary joint 24 and the Camper's joint 40.

Figure 5:
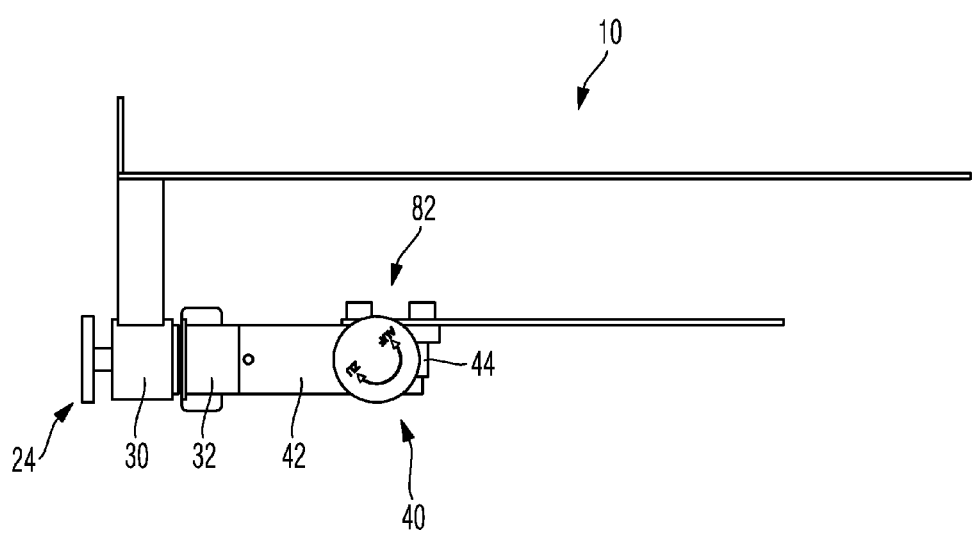
FIG. 5 shows the occlusion determination device according to FIG. 3 in a side view.

FIG. 5 illustrates a side view of an inventive occlusion determination device 10 from the left-hand side. The joint parts 30 and 32 are formed as cylindrical elements and are part of the bipupillary joint 24 in this respect. Part 42 of the Camper's joint 40 is also formed as a cylindrical element while part 44 is formed as a metal block on whose top side the connection surface of the alternating connection 82 is formed.

Figure 6:
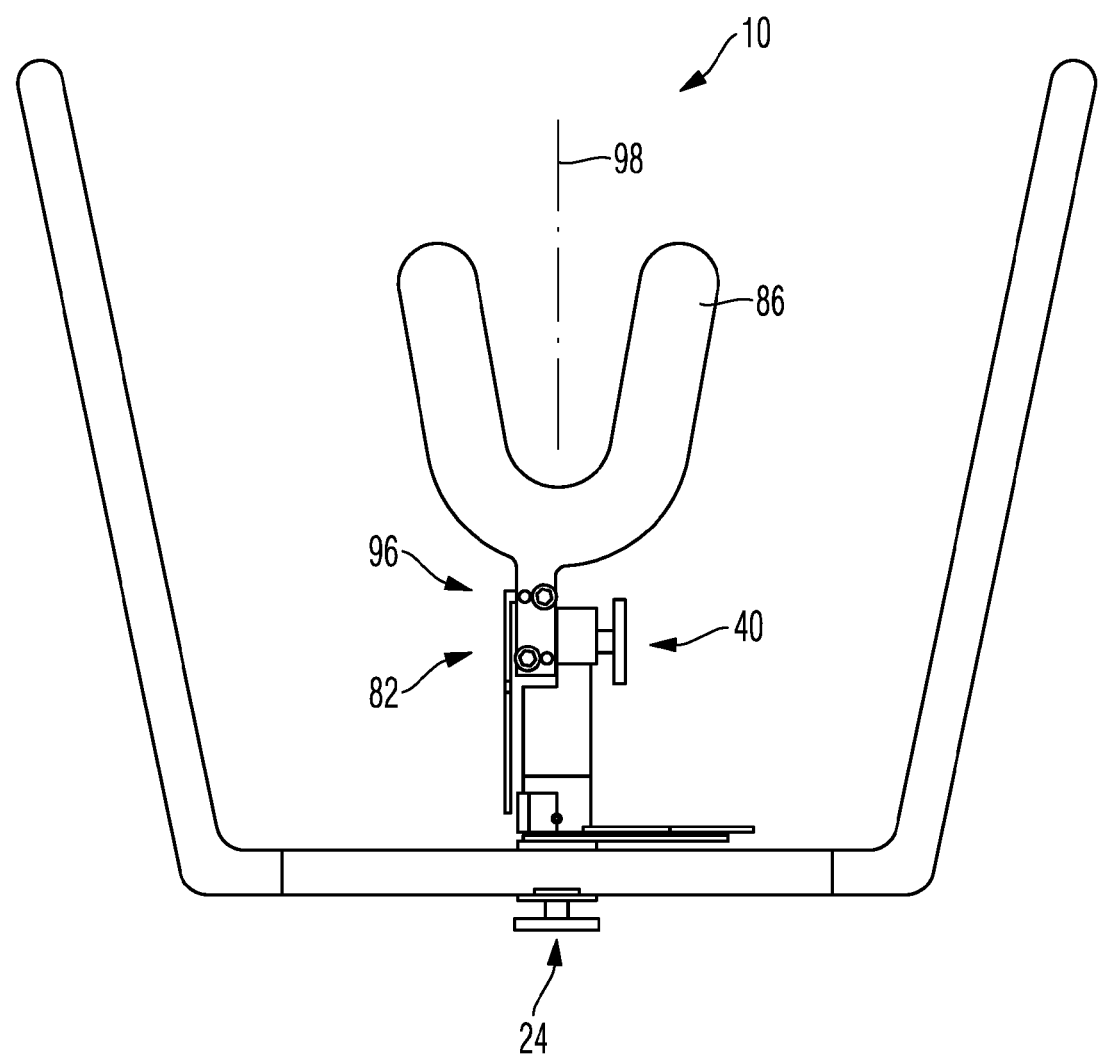
FIG. 6 shows the occlusion determination device according to FIG. 3 in a top view.

FIG. 6 shows an occlusion determination device 10 in a top view. As can be seen, a connection pin 96 of the alternating connection 82 is formed in a slightly asymmetrically offset way in order to account for the connection possibility at the Camper's joint 40. It is to be understood that the bipupillary joint 24 is designed to come to rest exactly in the sagittal plane 98.

Figure 7:
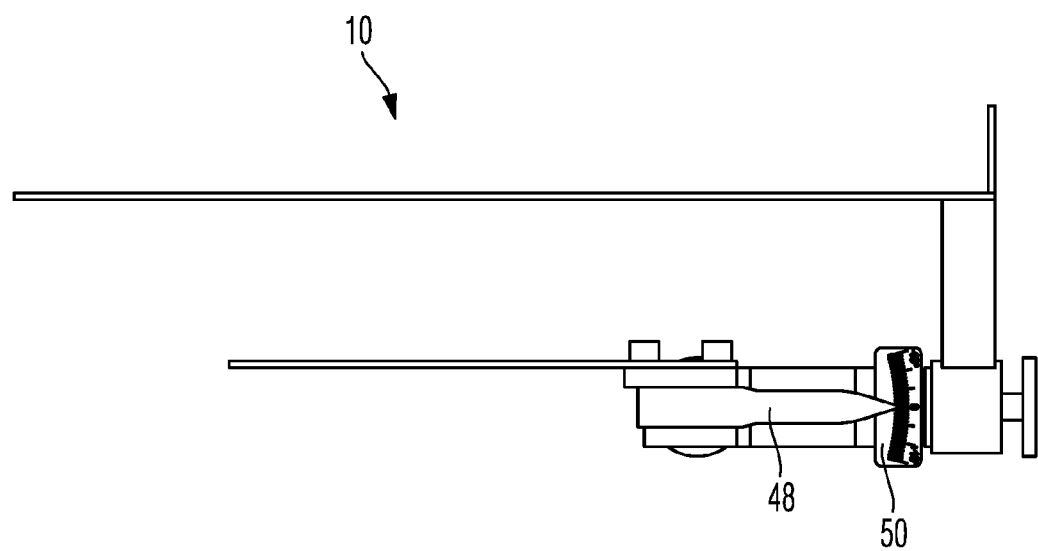
FIG. 7 shows the occlusion determination device according to FIG. 3 in another side view.

FIG. 7 illustrates a side view of the inventive occlusion determination device 10 from the right-hand side. Here, the scale 50 and the meter pointer 48 can be seen particularly well in the mutual arrangement; the angular position detected amounts to exactly 0°. The measuring angular range is in the range of between −15° and +15° wherein usually the relative arrangement of occlusal plane and Camper's plane deviate from one another by considerably less than +1520 or −15°.

The pivoting mobility of the Camper's joint can be limited by stops which limit the possible pivot angle in any desired way. For instance, a maximum pivot angle of +/−30° with regard to the horizontal center position can be provided but also a maximum pivot angle of +/−25° or only 20°. In any case, the pivot angle should facilitate pivoting in the range of the scale 50, and if the scale extends across a smaller range, such as between −7° and +9°, the pivot angle can also be limited correspondingly.

Figure 8:
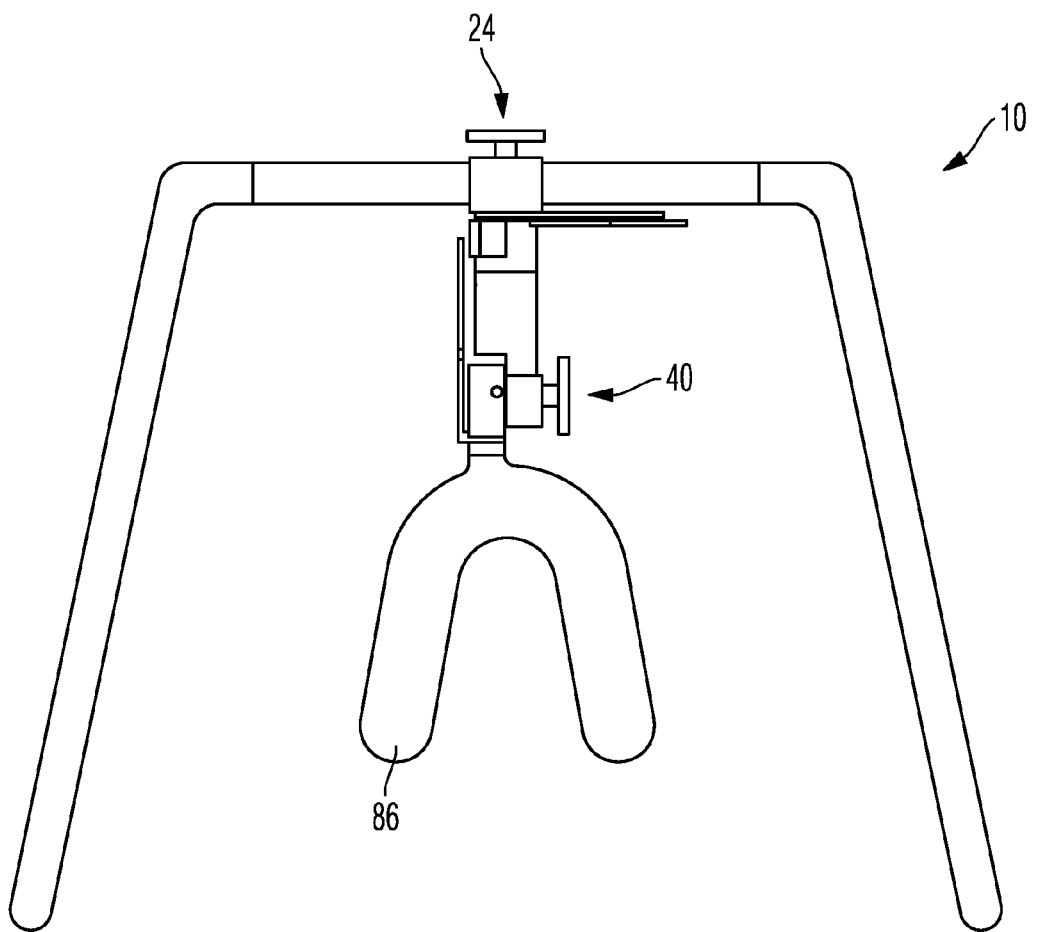
FIG. 8 shows the occlusion determination device according to FIG. 3 in a bottom view.

FIG. 8 shows a bottom view of the inventive occlusion determination device 10. Here, it can also be seen that the pivot axes of the Camper's joint 40 and the bipupillary joint 24 extend vertically to one another.

Figure 9:
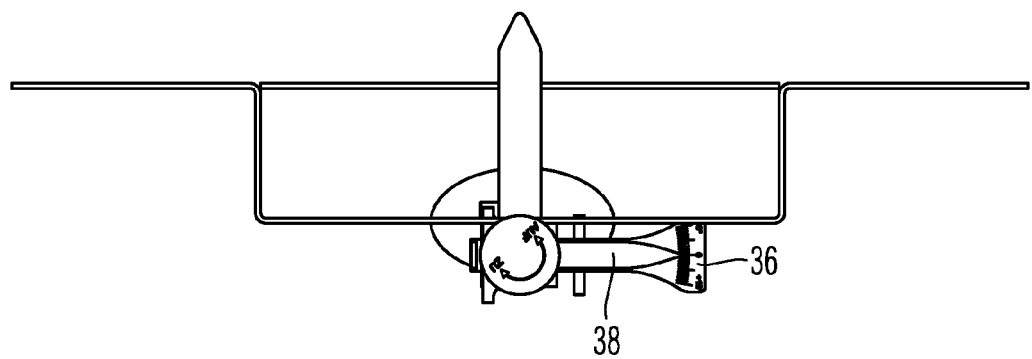
FIG. 9 shows the occlusion determination device according to FIG. 3 in a front view.

The relative arrangement of the meter pointer 38 and the scale 36 can be seen well from FIG. 9. Here, the registered indicating range amounts to between −10° and +10°, wherein here, too, the values which indeed occur in practice clearly fall within this range.

The bipupillary joint can also be provided with stops which limit the pivot range to values which are more generous than the indicating range of the scale 36, but a corresponding limitation is not necessary.

In a further embodiment of the invention the vertical distance between the bite frame 34 and the extraoral bracket 12 is adjustable. The adjustability can be implemented in a mechanically simple way but it is preferred to guide both elements in parallel. A corresponding solution can, for instance, be implemented using a scissor joint, like in civil engineering. Then, the adjustment range can be between 20 mm and 30 mm.

In a further advantageous embodiment reference elements are attached to the extraoral bracket 12, preferably to its side legs 12 and 16. By visual detection, these reference points are used to detect the position of the extraoral bracket—and thus of the occlusion determination device—for instance with the help of stereoscopic measures known per se, and thus the position of the occlusion determination device relative to the patient.

In a further advantageous embodiment it is provided to attach a labial shield at the bite frame 34. The reason for this is that in toothless jaws the upper lip of the patient often falls to the inside, and this is to be compensated for by the prothesis. The inventive upper labial shield or labial shield is used to ideally adjust or initially detect the position of the lip; then the prothesis which is later to be manufactured based on the result of the occlusion determination device determines the position of the lip, in particular by means of the horizontal position of the teeth and/or the configuration of the gingival material of the prothesis above the teeth which can be realized in a more or less protruding manner.

The labial shield can either be attached to the bite frame in a way firmly connected to the bite fork, or it can be mounted slidably relative to it, if necessary with a detectable position.

Figure 10:
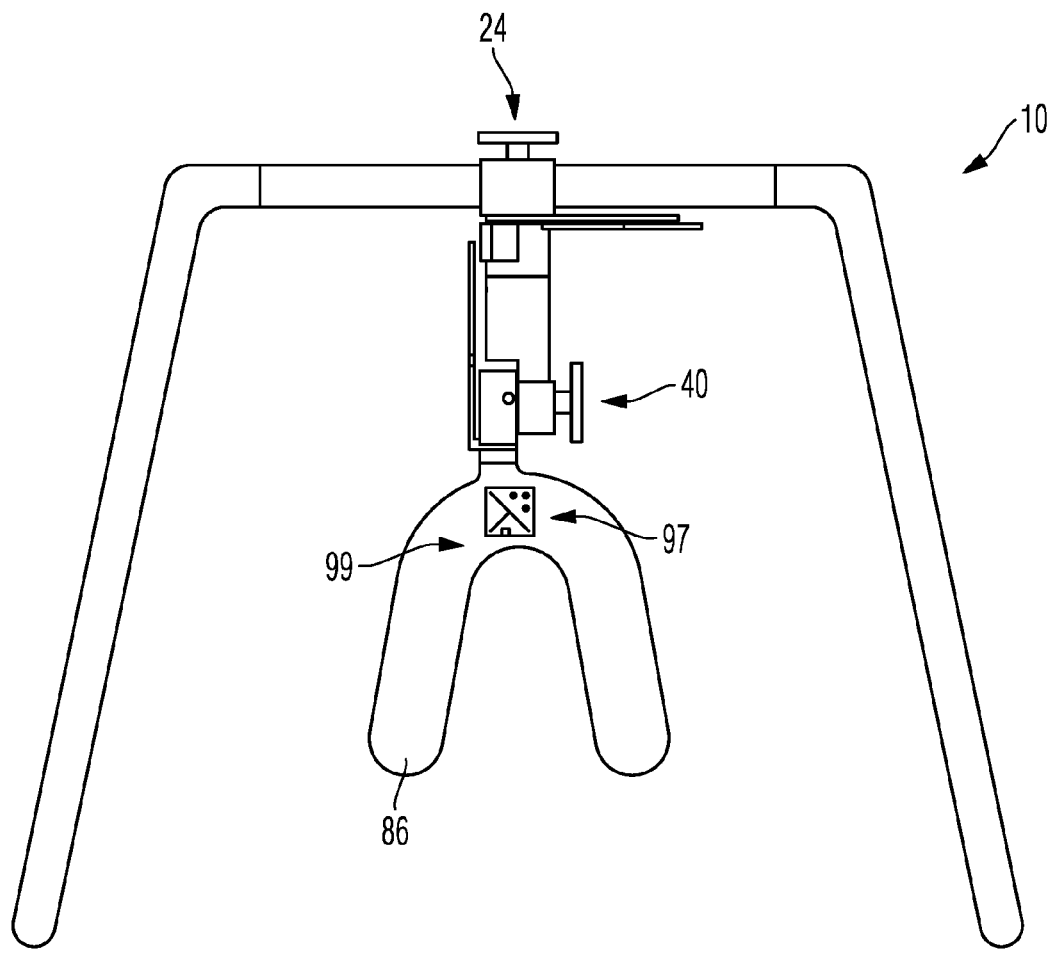
FIG. 10 shows a schematic top view of a further embodiment of an inventive occlusion determination device.

FIG. 10 shows how an occlusion determination reference element 97 can be attached which makes possible to exactly determine the position of the occlusion determination device when the bite fork is attached.

In order to determine the reference position, the impression compound can be used as a further auxiliary means after impression taking. In this way, an exact relationship between the position of the impression compound—and thus the jaw of the patient—and the extraoral bracket 12 can be obtained when an occlusion determination reference element is attached to the impression compound carrier—or possibly to the impression compound itself.

If no suitable occlusion determination reference element is used, there is the danger that the relative position of the occlusion determination device relative to the oral cavity of the patient is undetermined.

Thus, it is favorable according to the invention if not only the relative angles between the impression compound carrier or the bite fork on the one hand and the extraoral bracket 12 on the other hand can be determined, but also the position of the occlusion determination device with respect to the mouth of the patient with the help of the occlusion determination reference element 97, in particular in scanning operations.

However, three-dimensional scanning is particularly favorable for the production of a full denture.

Attaching the occlusion determination reference element 97 to the bite fork or the bite frame, or to the impression compound carrier, facilitates a very exact determination of reference, because if only one tool-holding fixture for the bite fork carries the reference element and the scan is thus effected based on said tool-holding fixture, inaccuracies when it comes to the mounting between the holder and the bite fork can distort the result of the scanning operation.

The reference element 97 can be configured in any desired manner. Preferably, it comprises a two-dimensional distinctive identification, and not a symmetrical cross or similar, for instance.

In an advantageous embodiment a resolution detection element 99 is provided which, for instance, consists of fine lines whose distinctiveness facilitates to make a statement about if a proper focusing on the occlusion determination reference element 97 has occurred.

The invention claimed is:

1. An occlusion determination device, comprising a bite frame and an extraoral bracket which are connected to one another, wherein a reference element comprises at least one vertical leg and at least one horizontal leg and is connected with the bite frame by way of a bipupillary joint,
   characterized in that the reference element is formed as an extraoral bracket which extends vertically offset from the bite frame,
   in addition to the bipupillary joint the occlusion determination device is provided with a Camper's joint, the joint axis of which is formed in a transverse manner relative to the bipupillary joint, which extends between the bite frame and the bipupillary joint, wherein a pin is disposed between the joints,
   at least one joint is provided with an angular detection device via which the angles of the parts of the occlusion determination device which are connected to one another by the joint and pivotable against each other are readable, and
   wherein the bipupillary joint allows for the adjustment of the angular position of the occlusal plane relative to the bipupillary line and the detection upon fixation.

2. The occlusion determination device according to claim 1, characterized in that the extraoral bracket comprises a vertical pointer which is connected to the extraoral bracket in a torque-proof manner and points to the top extending beyond the extraoral bracket.

3. The occlusion determination device according to claim 1, characterized in that the vertical distance between the bite frame and the extraoral bracket substantially corresponds to the distance between the occlusal plane and the Camper's plane of a patient.

4. The occlusion determination device according to claim 1, characterized in that an alternating connection is disposed at the bite frame for receiving either an impression compound carrier or a bite fork.

5. The occlusion determination device according to claim 1, characterized in that the joint axes of the bipupillary joint and the Camper's joint extend transversely to one another.

6. The occlusion determination device according to claim 5, characterized in that the joint axes of the bipupillary joint and the Camper's joint extend transversely at a right angle to one another.

7. The occlusion determination device according to claim 1, characterized in that the Camper's joint comprises stops which limit the deflection of the bite frame compared to the pin to a pivot angle of less than ±30 degrees.

8. The occlusion determination device according to claim 7, characterized in that the pivot angle is less than ±20 degrees.

9. The occlusion determination device according to claim 7, characterized in that the pivot angle is −17 to +9 degrees.

10. The occlusion determination device according to claim 1, characterized in that at least one joint comprises an opening and closing mechanism which is used to fix a predefined pivot position at the discretion of the user.

11. The occlusion determination device according to claim 10, characterized in that the opening and closing mechanism comprises a knurled nut.

12. The occlusion determination device according to claim 1, characterized in that at least one joint comprises a scale and a pointer via which the angular position is readable at a predefined rotary position.

13. The occlusion determination device according to claim 12, characterized in that in both joints, comprise a scale and a pointer via which the angular position is readable at a predefined rotary position.

14. The occlusion determination device according to claim 1, characterized in that the Camper's joint allows for the adjustment of the angular position of the occlusal plane relative to the Camper's plane and the detection upon fixation.

15. The occlusion determination device according to claim 1, characterized in that at least one vertically extending support leg is formed for the vertically offset mounting of the extraoral bracket to the bite frame.

16. The occlusion determination device according to claim 15, characterized in that the at least one support leg is part of a strip made of metal or sheet metal which forms the extraoral bracket.

17. The occlusion determination device according to claim 15, characterized in that at least two vertically extending support legs are formed for the vertically offset mounting of the extraoral bracket to the bite frame.

18. The occlusion determination device according to claim 1, characterized in that the vertical offset between the extraoral bracket and the bite frame is adjustable around a center position of 25 mm.

19. The occlusion determination device according to claim 18, wherein the vertical offset is adjustable from the center position of 25 mm to a point as far left as 18 mm or to a point as far right at 31 mm.

20. The occlusion determination device according to claim 1, characterized in that the extraoral bracket is counter-bent twice substantially at a right angle and forms the vertically extending support legs at this position.

21. The occlusion determination device according to claim 1, characterized in that the extraoral bracket at front/external edges, comprises joints having a vertical axis via which the side legs of the extraoral bracket are pivotable against one another.

22. The occlusion determination device according to claim 1, characterized in that the extraoral bracket supports at least one reference element at a predefined position via which the location of the extraoral bracket relative to the patient, can be detected by extracorporeal detection.

23. The occlusion determination device according to claim 1, characterized in that an occlusion determination reference element is attached to the occlusion determination device at a transition region between the bite frame and at least one of a center leg of a bite fork and a receptacle for at least one of an impression compound carrier and an impression compound carrier, which occlusion determination reference element allows for the detection of the translational position of the occlusion determination device in at least one of a scanning device and a digital articulator.

24. The occlusion determination device according to claim 1, wherein both the bipupillary joint and the Camper's joint are provided with an angular detection device via which the angles of the parts of the occlusion determination device which are connected to one another by the joint and pivotable against each other are readable.

* * * * *